US00PP15718P3

(12) United States Plant Patent
Trees

(10) Patent No.: US PP15,718 P3
(45) Date of Patent: Apr. 12, 2005

(54) ***VERBENA* PLANT NAMED 'BALAZCHERD'**

(50) Latin Name: *Verbena×hybrida*
Varietal Denomination: Balazcherd

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 35 days.

(21) Appl. No.: 10/741,415

(22) Filed: Dec. 19, 2003

(65) Prior Publication Data

US 2004/0226064 P1 Nov. 11, 2004

(51) Int. Cl.[7] ..... A01H 5/00

(52) U.S. Cl. ..... Plt./308

(58) Field of Search ..... Plt./308

*Primary Examiner*—Anne Marie Grunberg

(74) *Attorney, Agent, or Firm*—Wood, Phillips, Katz, Clark & Mortimer

(57) ABSTRACT

A new and distinct cultivar of *Verbena* plant named 'Balazcherd' characterized by its red-colored flowers, cleft, dark green-colored foliage, basal branching character, and mounded and trailing growth habit.

1 Drawing Sheet

Latin name of genus and species of plant claimed: *Verbena×hybrida.*
Variety denomination: 'Balazcherd'.

BACKGROUND OF THE INVENTION

The present invention relates to a new and distinct *Verbena* plant botanically known as *Verbena×hybrida* and hereinafter referred to by the cultivar name 'Balazcherd'.

The new cultivar was developed by the inventor through a controlled breeding program during January 2001 at Arroyo Grande, Calif. The objective of the breeding program was the development of *Verbena* cultivars with attractive flower coloration, continuous flowering and semi-trailing growth habit.

The female (seed) parent of 'Balazcherd' was the proprietary *Verbena×hybrida* cultivar designated 'BFP-1406' (not patented), which exhibits a prostrate, trailing habit, red-colored flowers and serrated, medium green-colored foliage. The male (pollen) parent of 'Balazcherd' was the proprietary *Verbena×hybrida* cultivar designated BFP-1040 (not patented), which exhibits an upright habit, dark red-colored flowers and medium green-colored foliage. The new cultivar was discovered and selected by the inventor as a single flowering plant from within the progeny of the above stated cross-pollination during 2001 at Arroyo Grande, Calif.

Asexual reproduction of the new cultivar by terminal stem cuttings since 2001 at West Chicago, Ill., has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any change in genotype.

It was repeatedly found that the cultivar of the present invention:

1. Exhibits red-colored flowers,
2. Forms cleft, dark green-colored foliage,
3. Exhibits a good basal branching character, and
4. Exhibits a mounded and trailing growth habit.

Plants of the new cultivar differ from plants of the female parent primarily in leaf type and leaf color and from plants of the male parent primarily in growth habit.

Of the many *Verbena* cultivars know to the inventor, the most similar to 'Balazcherd' is the cultivar 'Flamenco' (not patented). However, in side-by-side comparisons conducted in West Chicago, Ill., plants of the new cultivar differed from plants of the cultivar 'Flamenco' by the following characteristics:

1. Plants of the new cultivar have larger flowers than plants of the cultivar 'Flamenco', and
2. Plants of the new cultivar have a more spreading growth habit than plants of the cultivar 'Flamenco'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balazcherd'. The plants were grown in a greenhouse for nine weeks in West Chicago, Ill.

DETAILED BOTANICAL DESCRIPTION

Figure 1:
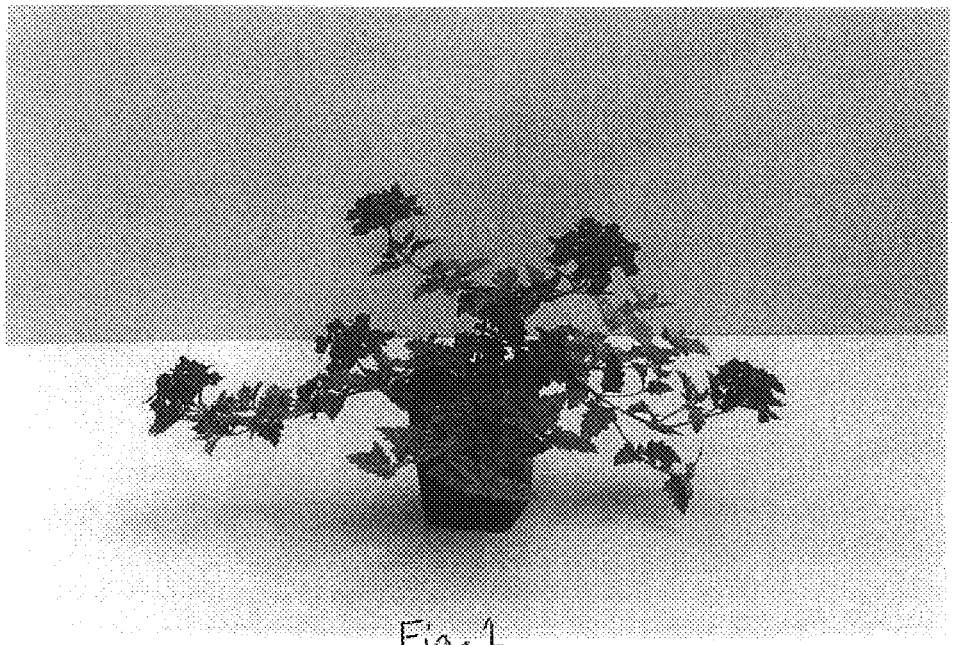
FIG. 1 illustrates a side view of the overall growth and flowering habit of 'Balazcherd'.
Figure 2:
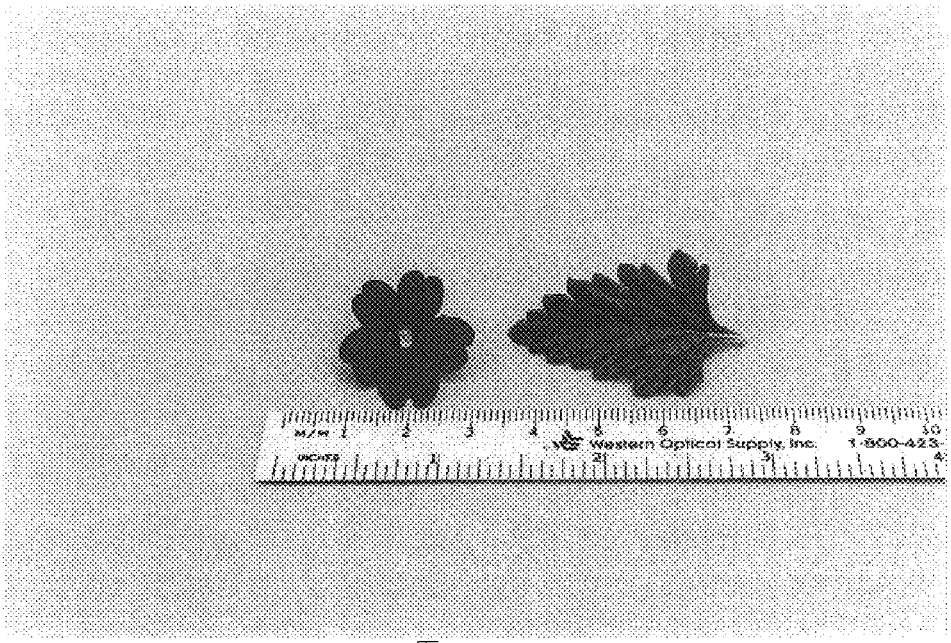
FIG. 2 illustrates a close up view of an individual flower and leaf of 'Balazcherd'.

The chart used in the identification of colors described herein is the R.H.S. Colour Chart of The Royal Horticultural Society, London, England, 1995 edition, except where general color terms of ordinary significance are used. The color values were determined on Jul. 16, 2003 in West Chicago, Ill. The readings were taken between 10:30 and 11:30 a.m. under natural light conditions. The plants used for the following descriptions and measurements were produced from cuttings taken from stock plants and were grown in a double polycarbonate covered greenhouse under conditions comparable to those used in commercial practice. The plants were grown in 10 cm pots for 9 weeks while utilizing a soilless growth medium. Greenhouse temperatures were maintained at approximately 70°–80° F. during the day and approximately 62°–65° F. during the night. Greenhouse light levels were maintained at 5,000–8,000 footcandles during the day.

Botanical classification: *Verbena×hybrida* cultivar 'Balazcherd'.

Parentage:

*Female parent.*—Proprietary *Verbena×hybrida* selection designated 'BFP-1406' (not patented).

*Male parent.*—Proprietary *Verbena×hybrida* selection designated 'BFP-1040' (not patented).

Propagation:

*Type cutting.*—Terminal stem.

*Time to initiate roots.*—Approximately 14–21 days.

*Root description.*—Fine, fibrous.

*Rooting habit.*—Freely branching.

Plant description:

*General appearance and growth habit.*—Spreading and trailing. Moderately vigorous with good basal branching. Pinching improves basal branching. A mature plant, 9 weeks after the planting of a rooted cutting, commonly measures approximately 13.2 cm in height and approximately 45 cm in diameter (area of spread).

*Branch description.*—Shape: Tetragonal. Diameter: Approximately 2 mm. Texture: Densely pubescent. Color: 146B. Internode length at middle of branch length is approximately 2.4 cm.

*Foliage.*—Type: Simple. Arrangement: Opposite. Shape: Ovate. Margin: Cleft. Apex: Broadly acute. Base: Attenuate. Texture: Densely covered with short stiff hairs on upper and lower surfaces, especially along veins on lower surface. Venation pattern: Pinnate. Leaf length: Approximately 3.7 cm. Leaf width: Approximately 2.3 cm at widest point. Upper surface of mature leaf is 137A, lower surface is 147B. Venation of upper and lower surface is 147C. Petiole: Length: Approximately 3.4 mm. Diameter: Approximately 2 mm. Texture: Pubescent with short stiff hairs on lower surface and glabrous on upper surface. Color of upper and lower surface: 147C.

Flowering description:

*Flowering habit.*—Freely flowering under outdoor growing conditions with substantially continuous blooming from spring through fall. Year round in greenhouse environment.

*Time to first flower.*—Approximately 5–7 weeks from planting of rooted cutting.

*Lastingness of individual bloom.*—Approximately 3–4 days.

Inflorescence description:

*Type.*—Hemispherical corymb positioned above and beyond foliage. Height: Approximately 3.4 cm. Width: Approximately 5.9 cm with approximately 16 fully opened flowers per inflorescence at any one time.

*Peduncle.*—Length: Approximately 4 cm. Diameter: Approximately 1.2 mm. Texture: Densely pubescent with short stiff hairs. Color: 147C.

Flower description:

*Type.*—Single, salverform, not fragrant, persistent.

*Bud.*—Shape: Club shaped. Length: 4.5 mm. Diameter: Approximately 6 mm. Color: 53C.

*Size.*—Corolla diameter: Approximately 2.4 cm. Corolla tube length: Approximately 1.9 cm. Tube diameter at opening: 2.2 mm. Tube diameter at base: 1 mm.

*Petals.*—Quantity: Five per flower, fused at base, somewhat overlapping. Shape: Obovate. Apex: Obtuse. Margin: Entire. Texture of upper and lower surface: Glabrous. Color when opening and when fully opened: Upper surface: 45B with 45A at base. Lower surface: 51B at apex, gradually changing to N155C at base. Whiskers of 155A surround the opening of the corolla tube.

*Corolla tube.*—Outside surface: Texture: Pubescent. Color: 145C. Inner surface: Texture: Pubescent around anthers. Color: 150D.

*Calyx.*—Quantity of sepals: 5, fused to form tube. Tube description: 5 toothed, 5 ribbed. Tube length: Approximately 1.4 cm. Tube diameter at base: Approximately 2 mm. Diameter at apex: Approximately 3 mm. Color: Ridges are 146C, valleys are 144D.

*Reproductive organs.*—Stamens: Quantity: 4 per flower. Anther shape: Ovoid. Anther length: 1 mm. Anther color: 151D. Pollen: None observed. Pistil: Quantity: One per flower. Pistil length: 2.7 cm. Stigma shape: Bi-lobed, funnel shaped. Stigma length: 4 mm. Stigma color: 144C. Style length: 2.2 cm. Style color: 144C. Ovary diameter: 1 mm. Ovary color: 144A.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balazcherd', substantially, as herein shown and described, which:

1. Exhibits red-colored flowers,
2. Forms cleft, dark green-colored foliage,
3. Exhibits a good basal branching character, and
4. Exhibits a mounded and trailing growth habit.

* * * * *